US006673066B2

(12) United States Patent
Werneth

(10) Patent No.: US 6,673,066 B2
(45) Date of Patent: Jan. 6, 2004

(54) APPARATUS AND METHOD TO DIAGNOSE AND TREAT VULNERABLE PLAQUE

(75) Inventor: Randell L. Werneth, Poway, CA (US)

(73) Assignee: Cardiostream, Inc., Poway, CA (US)

( * ) Notice: Subject to any disclaimer, the term of this patent is extended or adjusted under 35 U.S.C. 154(b) by 0 days.

(21) Appl. No.: 09/899,753

(22) Filed: Jul. 3, 2001

(65) Prior Publication Data

US 2002/0068928 A1 Jun. 6, 2002

Related U.S. Application Data

(60) Provisional application No. 60/246,951, filed on Nov. 10, 2000.

(51) Int. Cl.[7] .............................................. A61B 18/18
(52) U.S. Cl. ........................... 606/21; 128/898; 606/23
(58) Field of Search ..................... 606/20–26; 600/549; 128/898

(56) References Cited

U.S. PATENT DOCUMENTS

| 5,147,355 | A |   | 9/1992 | Friedman et al. .............. 606/23 |
| 5,868,735 | A | * | 2/1999 | Lafontaine ..................... 606/21 |
| 5,871,449 | A |   | 2/1999 | Brown .......................... 600/474 |
| 5,899,899 | A |   | 5/1999 | Arless et al. .................. 606/22 |
| 5,902,268 | A | * | 5/1999 | Saab ............................ 604/113 |
| 5,902,299 | A |   | 5/1999 | Jayaraman ..................... 606/20 |
| 5,906,636 | A |   | 5/1999 | Casscells, III et al. ........ 607/96 |
| 5,924,997 | A | * | 7/1999 | Campbell ..................... 600/505 |
| 5,935,075 | A |   | 8/1999 | Casscells et al. ............ 600/474 |
| 5,971,979 | A | * | 10/1999 | Joye et al. ................... 128/898 |
| 6,011,995 | A | * | 1/2000 | Guglielmi et al. ............ 607/99 |
| 6,106,518 | A |   | 8/2000 | Wittenberger et al. ......... 606/23 |
| 6,139,544 | A |   | 10/2000 | Mikus et al. .................. 606/21 |
| 6,161,049 | A |   | 12/2000 | Rudie et al. ................. 607/101 |
| 6,190,379 | B1 |   | 2/2001 | Heuser et al. |
| 6,203,508 | B1 |   | 3/2001 | Ren et al. ..................... 600/587 |
| 6,206,847 | B1 |   | 3/2001 | Edwards et al. ............... 604/22 |
| 6,228,109 | B1 | * | 5/2001 | Tu et al. ........................ 606/41 |
| 6,231,595 | B1 |   | 5/2001 | Dobak, III ................... 607/106 |
| 6,235,019 | B1 |   | 5/2001 | Lehmann et al. ............. 606/22 |
| 6,241,718 | B1 |   | 6/2001 | Arless et al. ................. 604/509 |
| 6,245,026 | B1 | * | 6/2001 | Campbell et al. ............ 600/549 |
| 6,251,129 | B1 |   | 6/2001 | Dobak, III et al. .......... 607/105 |
| 6,251,130 | B1 |   | 6/2001 | Dobak, III et al. .......... 607/105 |
| 6,283,959 | B1 | * | 9/2001 | Lalonde et al. ................ 606/21 |
| 6,295,680 | B1 |   | 10/2001 | Wahl et al. ...................... 14/1 |
| 6,312,452 | B1 |   | 11/2001 | Dobak, III et al. .......... 607/105 |
| 6,450,971 | B1 | * | 9/2002 | Andrus et al. ............... 600/549 |
| 6,451,011 | B2 | * | 9/2002 | Tu .............................. 128/898 |
| 2001/0007940 | A1 | * | 7/2001 | Lalonde et al. ................ 606/41 |
| 2001/0047138 | A1 | * | 11/2001 | Kokate et al. ............... 600/585 |
| 2002/0082515 | A1 | * | 6/2002 | Campbell et al. ............ 600/549 |

OTHER PUBLICATIONS

Stefanadis, Christodoulos et al., "Thermal Heterogeneity Within Human Atherosclerotic Coronary Arteries Detected In Vivo", Circulation, Apr. 20, 1999; pp. 1965–1971; vol. 99.
Stefandis, Christodoulos et al., "Increased Local Temperature in Human Coronary Atherosclerotic Plaques", Journal of the American College of Cardiology; Apr., 2001; pp. 1277–1283; vol. 37, No. 5.

* cited by examiner

Primary Examiner—Michael Peffley
(74) Attorney, Agent, or Firm—Gray Cary Ware & Freidenrich, LLP; Lisa A. Haile; June M. Learn

(57) ABSTRACT

The present invention may be embodied in a technique for elimination of vulnerable plaque in a vessel. Vulnerable plaque is detected in the vessel based on a temperature increase of the vessel's wall and treated using cryoablation.

16 Claims, 4 Drawing Sheets

APPARATUS AND METHOD TO DIAGNOSE AND TREAT VULNERABLE PLAQUE

CROSS REFERENCE TO RELATED APPLICATIONS

This application claims priority under 35 U.S.C. §119(e)(1) and 37 C.F.R. 1.78(a)(4) to U.S. provisional patent application serial No. 60/246,951 filed Nov. 10, 2000. The entire disclosure of U.S. provisional patent application serial No. 60/246,951 is incorporated herein by reference.

BACKGROUND OF THE INVENTION

1. Field of the Invention

The present invention relates to diagnosis and treatment of vulnerable plaque in blood vessels.

2. Description of the Prior Art

Current vessel treatments include angioplasty and placement of stents to treat a blockage of a vessel. A problem with current treatments is recurrent stenosis that may result in subsequent procedures. Vulnerable plaque rupture is believed to be the cause of death in a large percentage of patients suffering heart attack and stroke. Detection of vulnerable plaque is problematic because the vulnerable plaque may not be associated with arterial blockage.

Accordingly, there exists a need for an apparatus and related techniques for diagnosing and treating vulnerable plaque in blood vessels. The present invention satisfies these needs and provides further related advantages.

SUMMARY OF THE INVENTION

The present invention may be embodied in a method, and related apparatus, for elimination of vulnerable plaque in a vessel. In the method, vulnerable plaque is detected in the vessel, and the detected vulnerable plaque in the vessel is treated using cryoablation.

In more detailed features of the invention, the vulnerable plaque may be detected in the vessel based on an increase in vessel wall temperature indicative of vulnerable plaque. Treatment of the detected vulnerable plaque may include spraying the vulnerable plaque with a cooled fluid, such as saline having a temperature of about 0° C. The vulnerable plaque may be ablated using a subzero or cryogenic fluid.

The present invention also may be embodied in a catheter for vessel treatment having a temperature sensor for detecting a temperature increase on a vessel wall indicative of vulnerable plaque, and a balloon for performing cryoablation on the vessel wall for vulnerable plaque treatment. The temperature sensor may be a thermal sensing wire on a surface of the balloon, a thermal sensing polymer on a surface of the balloon, or an optical thermometer, such as an infrared thermometer, that is placed at a distal tip of the balloon and joined to a guidewire.

In more detailed features of the invention, the balloon may have multiple chambers, such as a first chamber for centering the catheter within the vessel, a second chamber for performing the cryoablation, and a third chamber for allowing blood to flow in the vessel past the catheter. The vessel may be a heart vessel or a corotid artery. The catheter may further include a first lumen for supporting the balloon, a second lumen for providing cryogenic fluid to the balloon to inflate the balloon, and a third lumen for returning cryogentic fluid from the balloon. The catheter may also include a larger marker near a distal end of the catheter for joining together the first lumen and the second lumen, and a smaller marker at a proximal area of the catheter for joining together the first lumen, the second lumen, and the third lumen

BRIEF DESCRIPTION OF THE DRAWINGS

The accompanying drawings illustrate embodiments of the present invention and, together with the description, serve to explain the principles of the invention.

DETAILED DESCRIPTION

The present invention may be embodied in an apparatus, and related method, for diagnosing and treating vulnerable plaque in vessels. Vulnerable plaque is defined as a lipid-rich atheromatous core, covered by a fibrous cap, and the presence of on-going inflammation within and underneath the cap. As inflammation reactions occur in the atheromatous core and in the thin-film fibrotic cap, a local increase in temperature in the vessel may occur.

Thermography may provide a technique to diagnose the vulnerable plaque. Application of cryoenergy to the vulnerable plaque may provide a technique to deactivate the inflammatory response and thus stabilize the associated lesion. The application of cryoenergy to the vulnerable plaque creates an injury in the vessel that destroys the cellular messenger apparatus of the mitochondria while preserving the anhydrous structure of the cellular matrix. Cryoenergy may eradicate components of the vulnerable plaque and allow a natural healing by migration of normal smooth muscle cells from regions adjacent to the treatment site.

Figure 1:
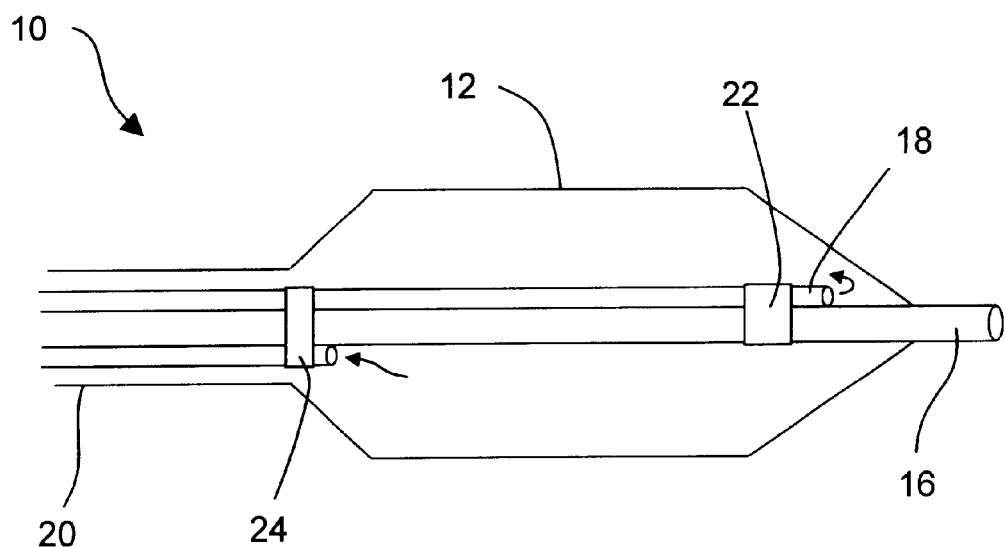
FIG. 1 shows a cross-sectional elevation view of a device for diagnosing and treating vulnerable plaque, according to the present invention.
Figure 2:
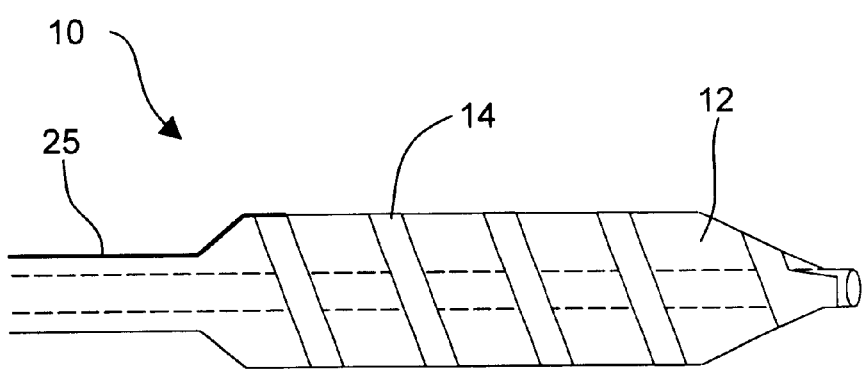
FIG. 2 shows an elevation view of the device for diagnosing and treating vulnerable plaque of FIG. 1, according to the present invention.

With reference to FIGS. 1 and 2, a device for diagnosis and treatment of vulnerable plaque of the present invention may be embodied in a catheter 10 having a balloon 12 (FIG. 1) integrated with a temperature sensor 14 (FIG. 2). The balloon is near the end of three lumens, 16, 18 and 20. The first lumen 16 is a larger lumen for support of the balloon and temperature sensor. The second lumen 18 provides a flow of cryogenic fluid to inflate the balloon. The third lumen 20 provides a return for the cryogenic fluid from the balloon. A large marker band 22 at the distal tip of the catheter joins the first and second lumens together. A small marker 24 at the proximal area joins the three lumens together. The balloon may be thermal sensing using a thermal sensing polymer on its surface or using an electronic integrated sensor such as a sensing wire for detecting the vessel's temperature. An outer-tubing conductor 25 may conduct an electric signal to the balloon and the inner-most tubing (first lumen 16) may conduct the signal back to an external instrument. Once the vulnerable or hot plaque is detected and confirmed, the balloon may be inflated with sub-zero fluid to deliver the cryoenergy treatment.

Pre-spraying of the vulnerable plaque may help condition the area for desired hypothermia treatment. After performing an endolumenial spraying of the area of the vulnerable plaque with 0° C. saline, the balloon may be inflated with subzero fluid to finish the treatment to the hot plaque.

Figure 3:
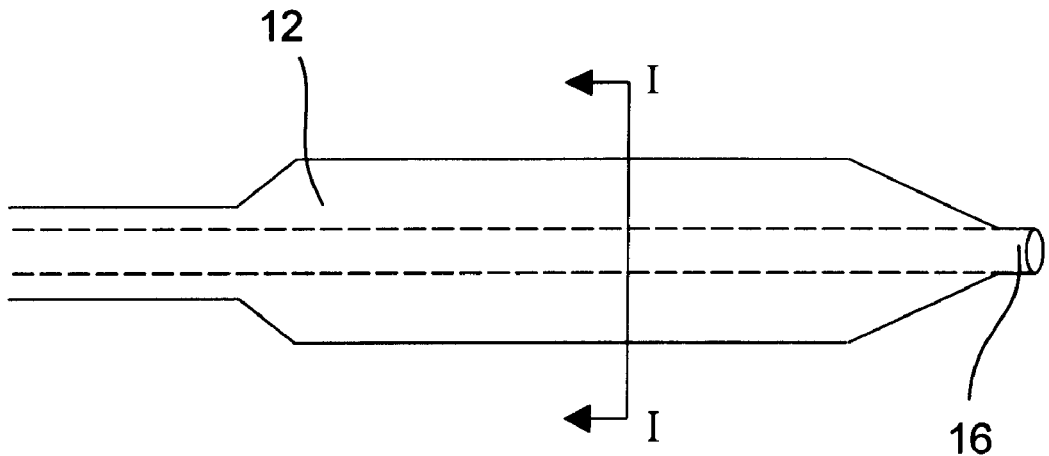
FIG. 3 shows an elevation view of another device for treating vulnerable plaque, according to the present invention.
Figure 4:
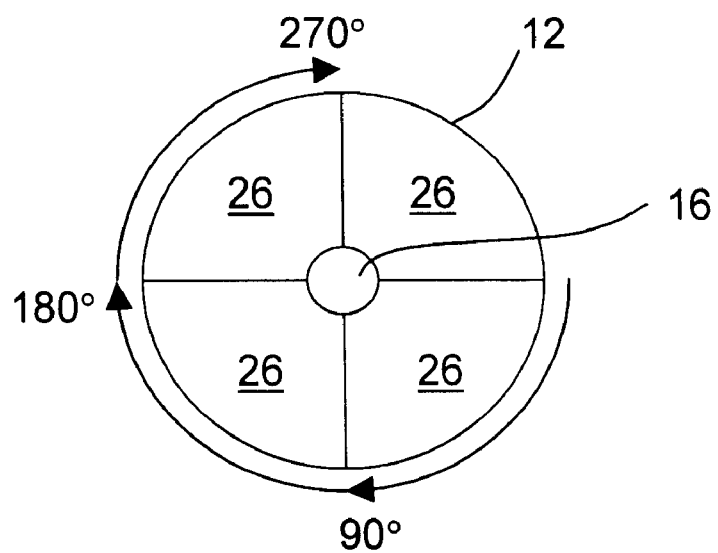
FIG. 4 shows a cross-sectional elevation view of the device for treating vulnerable plaque of FIG. 3, along a line I—I.

With reference to FIGS. 3 and 4, a device for diagnosis and treatment of vulnerable plaque may be embodied in a catheter 10 that allows blood to flow past the ablation device. The balloon 12 may have at least two chambers 26. At least one chamber is for keeping the device centered with in the vessel. Another chamber would be for filling with very cold fluid for ablation of the vulnerable plaque. The ablation chamber would cover at least 90°, and up to 270°, about a central axis of the device. Another chamber would not be inflated to allow blood to flow past the device. The multi-chambered balloon may allow for cryoenergy to be applied in the selected chamber if a treatment over a full 360° of the device is not desired.

Figure 5:
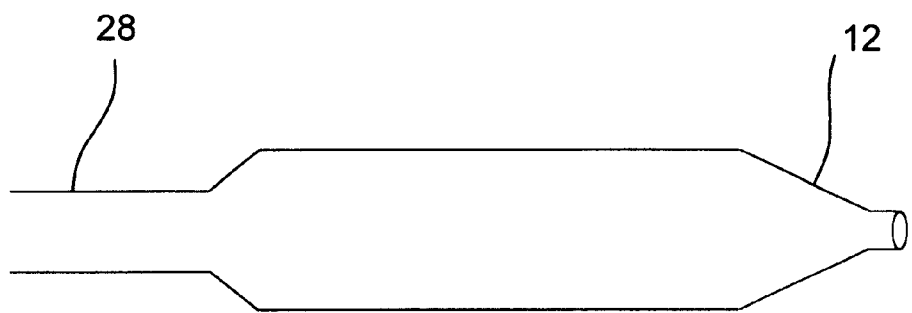
FIG. 5 shows an elevation view of another device for diagnosing and treating vulnerable plaque, according to the present invention.
Figure 6:
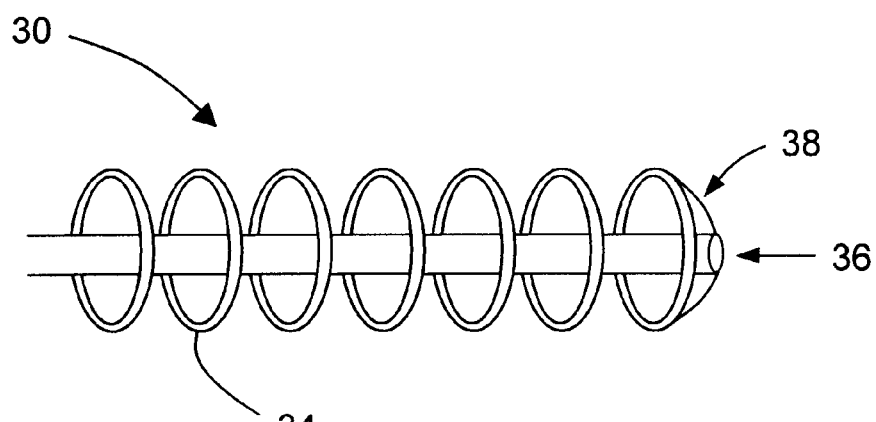
FIG. 6 shows an elevation view of a sensing tube for another device for diagnosing and treating vulnerable plaque, according to the present invention.

With reference to FIG. 5, the balloon 12 and outer shaft 28 may include a thermal sensing material. The balloon and outer shaft may be manufactured using conventional methods and then coated or plated with a material that is thermal sensing and conductive. The coated/plated balloon may be bonded to the outer shaft to connect the balloon with an electronic box that may read an output from the balloon. Thus, the angioplasty balloon may include a thermal sensing device and deliver the cryoenergy resulting in a catheter design that may be used for both diagnosis and treatment of vulnerable plaque.

Figure 7:
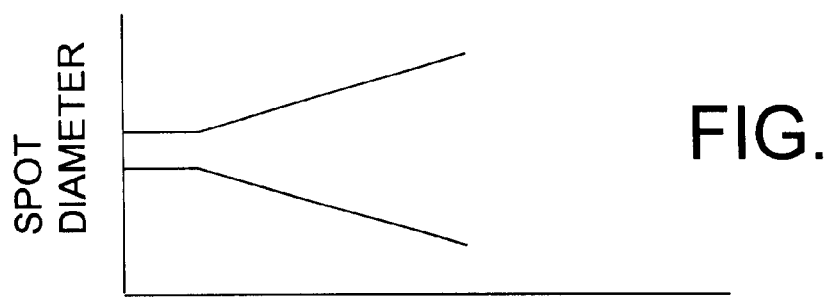
FIG. 7 shows a graph of a spot size versus distance for the sensing tube of FIG. 6.
Figure 8:
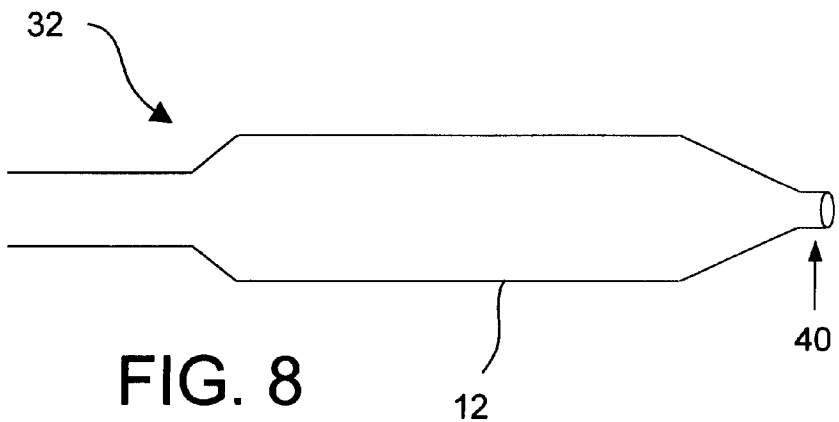
FIG. 8 shows an elevation view of an outer tube for a device for diagnosing and treating vulnerable plaque, according to the present invention.
Figure 9:
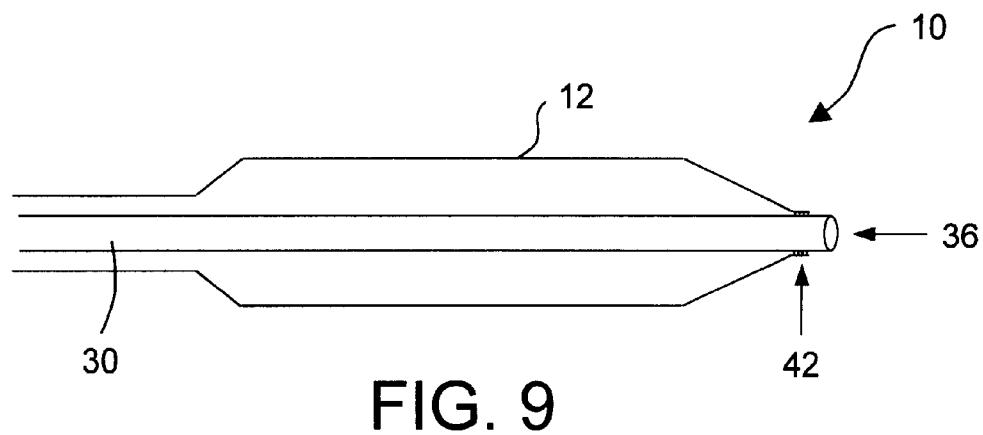
FIG. 9 shows an elevation view of a device for diagnosing and treating vulnerable plaque, according to the present invention.

With reference to FIGS. 6–9, a device for diagnosis and treatment of vulnerable plaque may be embodied in a catheter 10 (FIG. 9) that includes an inner tube 30 (FIG. 6) having a guide wire design and an infrared thermometer, and an outer tube 32 (FIG. 8) that may be similar to an angioplasty balloon. The inner tube may include an outer spiral wire 34, or coil, and an optical core 36. A weld joint 38 at the distal end of the inner tube connects the spiral wire to the optical core. A spot diameter increases with increasing distance between the tip of the sensor and a vessel wall as shown in FIG. 7. The outer tube includes a balloon 12 and a distal tip 40 with a seal. The inner tube with the guide wire is located within the outer tube and a seal 42 is formed at the distal end between the inner tube and the outer tube such that the optical core 36 is exposed at the distal end of the catheter.

The thermal wire may be placed in vascular anatomy if temperature is out of range and treatment is desired. The outer tubing balloon may be place over the inner-tubing.

Figure 10:
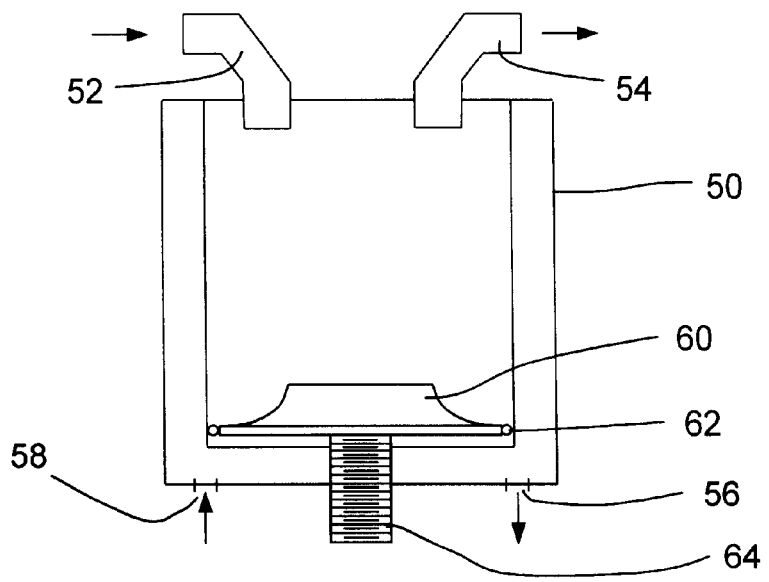
FIG. 10 shows an elevation view of a chamber for use in a device for diagnosing and treating vulnerable plaque.

With reference to FIG. 10, the delivery of the cryogenic fluid to the balloon 12 of the catheter 10 may be controlled by providing a chamber 50 (in an instrument console) that is sized to hold exactly the right amount of fluid for performing one cryotherapy cycle. The circulating coolant chamber includes a fluid-in and air-release port 52, a fluid-out port 54, a coolant-out port 56, a coolant-in port 58, and a plunger 60 having an O-ring 62 or similar type seal for separating the circulating coolant and the therapy fluid. The plunger is mounted on a screw 64 to advance the plunger for pumping the fluid out of the chamber. When application of the therapy is desired, the fluid is pumped from the chamber and through the catheter. The cryo-balloon then inflates for a period of time corresponding a period time for completely emptying the chamber. Once the fluid is pumped through the catheter, it may be pumped back into a holding chamber that re-chills the fluid to an appropriate cryogenic temperature. If a second inflation of the balloon is needed, the pre-cooled fluid may be pumped back into the delivery chamber.

The pump 50, tubing, a heat exchange unit, and all components contained in a chiller unit that are in direct contact with the fluid that circulates in and out of the catheter 10 may be self sterilized by the chiller unit. The tubing and the pump head may be formed of stainless steel. The chiller unit may circulate a solution of Betadyne® solution or similar fluid through the components. Alternatively, the chiller unit may circulate a fluid that heats the components to an appropriate temperature for sterilization.

In addition to treatment of heart vessels, cryotherapy techniques of the invention may benefit carotid angioplasty and stenting. The cryotherapy techniques may reduce the occurrence of second carotid endarterectomy (CEA) in cases of recurrent carotid artery stenosis.

While the invention has been illustrated and described in detail in the drawings and foregoing description, it should be understood the invention may be implemented though alternative embodiments within the spirit of the invention. Thus, the scope of the invention is not intended to be limited to the illustration and description in this specification, but is to be defined by the appended claims.

We claim:

1. A catheter for vessel treatment, comprising:
   a temperature sensor for detecting a temperature increase on a vessel wall indicative of the location of a vulnerable plaque;
   a balloon for performing cryoablation on the vessel wall for vulnerable plaque treatment so as to inhibit inflammatory response in the vulnerable plaque while preserving anhydrous cellular structure thereof;
   a first lumen for supporting the balloon;
   a second lumen for providing cryogenic fluid to the balloon to inflate the balloon;
   a third lumen for returning cryogentic fluid from the balloon;
   a larger marker near a distal end of the catheter for joining together the first lumen and the second lumen; and
   a smaller marker at a proximal area of the catheter for joining together the first lumen, the second lumen, and the third lumen.

2. A catheter for vessel treatment as defined in claim 1, wherein the temperature sensor is a thermal sensing wire.

3. A catheter for vessel treatment as defined in claim 2, wherein the thermal sensing wire is on a surface of the balloon.

4. A catheter for vessel treatment as defined in claim 1, wherein the temperature sensor is a thermal sensing polymer on a surface of the balloon.

5. A catheter for vessel treatment as defined in claim 1, wherein the temperature sensor is an optical thermometer that is placed at a distal tip of the balloon.

6. A catheter for vessel treatment as defined in claim 5, wherein the optical thermometer is an infrared thermometer.

7. A catheter for vessel treatment as defined in claim 5, further comprising a guidewire joined to the optical thermometer.

8. A catheter for vessel treatment as defined in claim 1, wherein the balloon has multiple chambers.

9. A catheter for vessel treatment as defined in claim 1, wherein the balloon has a first chamber for centering the catheter within the vessel, a second chamber for performing the cryoablation, and a third chamber for allowing blood to flow in the vessel past the catheter.

10. A catheter for vessel treatment as defined in claim 1, wherein the vessel is a heart vessel.

11. A catheter for vessel treatment as defined in claim 1, wherein the vessel is a carotid artery.

12. A method for vessel treatment, comprising the steps of:

detecting the location of a vulnerable plaque in a vessel; and treating the detected vulnerable plaque in the vessel using cryoablation so as to inhibit inflammatory response in the vulnerable plaque while preserving anhydrous cellular structure of the vulnerable plaque.

13. A method for vessel treatment as defined in claim 12, wherein vulnerable plaque is detected in the vessel based on an increase in vessel wall temperature indicative of vulnerable plaque.

14. A method for vessel treatment as defined in claim 12, wherein the step of treating the detected vulnerable plaque includes spraying the vulnerable plaque with a cooled fluid.

15. A method for vessel treatment as defined in claim 14, wherein the cooled fluid is saline having a temperature of about 0° C.

16. A method for vessel treatment as defined in claim 12, wherein the step of treating the detected vulnerable plaque includes ablating the vulnerable plaque using a subzero fluid.

* * * * *